(12) United States Patent
Yamaguchi et al.

(10) Patent No.: US 7,092,099 B2
(45) Date of Patent: Aug. 15, 2006

(54) MICROCHEMICAL SYSTEM AND PHOTOTHERMAL CONVERSION SPECTROSCOPIC ANALYSIS METHOD IMPLEMENTED BY THE SYSTEM

(75) Inventors: Jun Yamaguchi, Tokyo (JP); Akihiko Hattori, Osaka (JP); Takehiko Kitamori, Tokyo (JP); Manabu Tokeshi, Kanagawa (JP)

(73) Assignees: Nippon Sheet Glass Co., Ltd., Osaka (JP); Kanagawa Academy of Science & Technology, Kawasaki (JP)

( * ) Notice: Subject to any disclaimer, the term of this patent is extended or adjusted under 35 U.S.C. 154(b) by 220 days.

(21) Appl. No.: 10/766,582

(22) Filed: Jan. 27, 2004

(65) Prior Publication Data

US 2004/0257575 A1  Dec. 23, 2004

Related U.S. Application Data

(63) Continuation of application No. PCT/JP02/07552, filed on Jul. 25, 2002.

(30) Foreign Application Priority Data

Jul. 27, 2001 (JP) ............................. 2001-227713

(51) Int. Cl.
*G01N 21/00* (2006.01)
(52) U.S. Cl. .................................. 356/432; 356/432
(58) Field of Classification Search ................ 356/432, 356/430, 442, 317, 319; 359/244, 289, 299, 359/350, 288
See application file for complete search history.

(56) References Cited

U.S. PATENT DOCUMENTS

| | | | | |
|---|---|---|---|---|
| 4,927,268 A | * | 5/1990 | Carr et al. | 356/336 |
| 4,938,593 A | * | 7/1990 | Morris et al. | 356/344 |
| 5,513,006 A | * | 4/1996 | Schulz et al. | 356/432 |
| 6,452,710 B1 | * | 9/2002 | Hiraga et al. | 359/244 |
| 2003/0002038 A1 | * | 1/2003 | Mawatari | 356/300 |

FOREIGN PATENT DOCUMENTS

| | | | |
|---|---|---|---|
| DE | 427943 A1 | * | 5/1991 |
| EP | 1 087 223 A1 | | 3/2001 |
| JP | 8-178897 A | | 7/1996 |
| JP | 8-248266 A | | 9/1996 |
| JP | 10-232210 A | | 9/1998 |

(Continued)

OTHER PUBLICATIONS

Related U.S. Appl. No. 10/830,284, filed Apr. 21, 2004; Inventor: Jun Yamaguchi et al.; Title: Microchemical System, and Photothermal Conversion Spectroscopic Analysis Method.

*Primary Examiner*—Layla G. Lauchman
(74) *Attorney, Agent, or Firm*—Frishauf, Holtz, Goodman & Chick, P.C.

(57) ABSTRACT

A microchemical system is provided, which can improve the working efficiency of the user. In the microchemical system 1, a plate-shaped element 10 that constitutes an optical unit 1a has an optical wave guide path 20, which acts as an optical path for exciting light and detecting light. An irradiation lens 30 is disposed at an end of the optical wave guide path 20 downstream in the direction of travel of the exciting light and the detecting light, and a channel 40 is located downstream of the irradiation lens 30, through which a liquid containing a sample flows. A detector 50 is disposed at an end of the plate-shaped element 10 downstream of the channel 40 and detects the detecting light for analysis of the sample.

9 Claims, 9 Drawing Sheets

FOREIGN PATENT DOCUMENTS

| | | |
|---|---|---|
| JP | 2000-2677 A | 1/2000 |
| JP | 2001-59829 A | 3/2001 |

* cited by examiner

US 7,092,099 B2

MICROCHEMICAL SYSTEM AND PHOTOTHERMAL CONVERSION SPECTROSCOPIC ANALYSIS METHOD IMPLEMENTED BY THE SYSTEM

This application is a Continuation Application of International Application PCT/JP02/07552 filed Jul. 25, 2002.

TECHNICAL FIELD

The present invention relates to a microchemical system and a photothermal conversion spectroscopic analysis method implemented by the system.

BACKGROUND ART

Conventionally, in consideration of the rapidity of chemical reactions, and the need to carry out reactions using very small amounts, on-site analysis and the like, integration technology for carrying out chemical reactions in very small spaces has been focused upon, and research into this technology has been carried out with vigor throughout the world.

An example of such integration technology for carrying out chemical reactions is so-called microchemical systems that carry out mixing, reaction, separation, extraction, detection or the like on a sample placed in a very narrow channel which is formed in a small glass substrate or the like. Examples of reactions carried out in the microchemical systems include diazotization reactions, nitration reactions, and antigen-antibody reactions. Examples of extraction/separation include solvent extraction, electrophoretic separation, and column separation. Such a microsystem may use only a single function intended to carry out separation alone, or may use a plurality of functions in combination.

As an example in which 'separation' is the sole aim, out of the above functions, an electrophoresis apparatus for analyzing extremely small amounts of proteins, nucleic acids or the like has been proposed (e.g. Japanese Laid-open Patent Publication (Kokai) No. 8-178897). This electrophoresis apparatus analyzes extremely small amounts of proteins, nucleic acids or the like and is provided with a channel-formed plate-shaped element comprised of two glass substrates joined together. Because the element is plate-shaped, breakage is less likely to occur than in the case of a glass capillary tube having a circular or rectangular cross section, and hence handling is easier.

In these microchemical systems, because the amount of the sample is very small, a high-precision detection method is essential. The path to making a detection method of the required precision fit for practical use has been opened up through the establishment of a photothermal conversion spectroscopic analysis method which utilizes a thermal lens effect that is produced through a liquid-borne sample absorbing light in a very narrow channel.

When light is convergently irradiated onto a sample, the temperature of a solvent is locally increased by thermal energy emitted due to light absorbed by a solute in the sample to cause a change in the refractive index and hence generate a thermal lens (photothermal conversion effect). The photothermal conversion spectroscopic analysis method utilizes this photothermal conversion effect.

FIG. 6 is a view useful in explaining the principle of a thermal lens.

In FIG. 6, a convergent beam of exciting light is irradiated onto an extremely small sample via an objective lens of a microscope, whereupon the photothermal conversion effect takes place. In the sample onto which the convergent beam of exciting light is irradiated, the center of the convergent beam of exciting light is where the temperature rise is highest, and hence the rise rate of the temperature is greater toward the center of the convergent beam of exciting light, whereas the rise rate of the temperature is smaller with increasing distance from the center of the convergent beam of exciting light due to thermal diffusion. For most substances, the refractive index drops as the temperature rises, and hence the drop rate of the refractive index of the sample is greater toward the center of the convergent beam of exciting light, whereas the drop rate of the refractive index of the sample is smaller with increasing distance from the center of the convergent beam of exciting light. Optically, this pattern of change in the refractive index brings about the same effect as with a concave lens, and hence the effect is called the thermal lens effect. The size of the thermal lens effect, i.e. the power of the thermal lens is proportional to the optical absorbance of the sample. Moreover, in the case that the refractive index increases with temperature, a converse effect to the above, i.e. the same effect as a convex lens is produced.

In the photothermal conversion spectroscopic analysis method described above, thermal diffusion in a sample, i.e. change in refractive index of the sample, is observed, and hence the method is suitable for detecting concentrations in extremely small amounts of samples.

A photothermal conversion spectroscopic analyzer that uses the photothermal conversion spectroscopic analysis method described above has been proposed by Japanese Laid-open Patent Publication (Kokai) No. 10-232210.

In the conventional photothermal conversion spectroscopic analyzer, a channel-formed plate-shaped element is disposed below the objective lens of a microscope, and exciting light of a predetermined wavelength outputted from an exciting light source is introduced into the microscope. The exciting light is thus convergently irradiated via the objective lens onto a sample in the channel of the channel-formed plate-shaped element. Thus, a thermal lens is formed about the convergent irradiation position in which the exciting light is convergently irradiated.

Moreover, detecting light having a wavelength different to that of the exciting light is outputted from a detecting light source and also introduced into the microscope and then emitted therefrom. The detecting light emitted from the microscope is convergently irradiated onto the thermal lens that has been formed in the sample by the exciting light. Then, the detecting light passing through the sample is either diverged or converged due to the effect of the thermal lens. The diverged or converged light exiting the sample passes as signal light through a converging lens and a filter or just a filter, and is then received and detected by a detector. The intensity of the detected signal light depends on the refractive index of the thermal lens formed in the sample. The detecting light may have the same wavelength as that of the exciting light, or the exciting light may be used as the detecting light as well.

In the spectroscopic analyzer described above, a thermal lens is thus formed at the focal position of the exciting light, and the change in refractive index within the formed thermal lens is detected by means of detecting light.

In the above photothermal conversion spectroscopic analyzer, the light source, measuring section and detecting section (photothermal conversion section) have complicated optical systems and hence are large in size and lacks portability. Thus, in carrying out analysis or handling chemical reactions using the photothermal conversion spectroscopic analyzer, there are limitations on the place for installing the analyzer and the operation of the analyzer, and even the working efficiency of the user is degraded.

Further, in the above photothermal conversion spectroscopic analyzer, the exciting light and the detecting light are guided in the air to the sample, and therefore, optical elements such as the light source, mirrors, and lenses are fixed to a solid surface table to prevent these optical elements from moving during measurement. Moreover, in the case that the optical axes of the exciting light and the detecting light are shifted due to environmental changes such as temperature change, a jig is required for correcting the shifting. These also constitute factors of the increased size of the photothermal conversion spectroscopic analyzer and the lack of portability of the same.

In a microchemical system using the photothermal conversion spectroscopic analysis method, in most cases, it is required that the focal position of the exciting light and that of the detecting light should be different from each other. FIGS. 7A and 7B are views useful in explaining the formation position of the thermal lens and the focal position of the detecting light in the direction of travel of the exciting light. FIG. 7A shows a case in which the objective lens has chromatic aberration, whereas FIG. 7B shows a case in which the objective lens does not have chromatic aberration.

In the case that the objective lens 130 has chromatic aberration, a thermal lens 131 is formed at the focal position 132 of the exciting light as shown in FIG. 7A. The focal position 133 of the detecting light is shifted by an amount ΔL from the focal position 132 of the exciting light, and thus changes in the refractive index within the thermal lens 131 can be detected as changes in the focal distance of the detecting light from the detecting light. In the case that the objective lens 130 does not have chromatic aberration, on the other hand, the focal position 133 of the detecting light is almost exactly the same as the position of the thermal lens 131 formed at the focal position 132 of the exciting light, as shown in FIG. 7B. The detecting light is thus not deflected by the thermal lens 131, and hence changes in the refractive index within the thermal lens 131 cannot be detected.

However, the objective lens of a microscope is generally manufactured so as not to have chromatic aberration, and hence the focal position 133 of the detecting light is almost exactly the same as the position of the thermal lens 131 formed at the focal position 132 of the exciting light as described above, as shown in FIG. 7B. Changes in the refractive index within the thermal lens 131 thus cannot be detected. There is thus a problem that trouble must be taken to either shift the position in which the thermal lens 131 is formed from the focal position 133 of the detecting light every time a measurement is taken as shown in FIGS. 8A and 8B, or else angle the detecting light slightly using a lens (not shown) before passing the detecting light through the objective lens 130 so that the focal position 133 of the detecting light will be shifted from the thermal lens 131 as shown in FIG. 9. This also leads to degraded working efficiency of the user.

It is an object of the present invention to provide a microchemical system and a photothermal conversion spectroscopic analysis method implemented by the microchemical system which enable working efficiency of the user to be improved, and also provide a microchemical system which can be made smaller in size.

SUMMARY OF THE INVENTION

To attain the above object, in a first aspect of the present invention, there is provided a photothermal conversion spectroscopic analysis method of analyzing a sample by irradiating exciting light and detecting light via an irradiation lens, and detecting the detecting light passing through a thermal lens generated by the sample onto which the exciting light has been irradiated, characterized in that the exciting light and the detecting light are guided in a single mode to the irradiation lens via an optical wave guide path.

To attain the above object, in a second aspect of the present invention, there is provided a microchemical system comprising an exciting light source that outputs exciting light, a detecting light source that outputs detecting light, a guide optical system that guides the exciting light and the detecting light together, an irradiation lens that irradiates the exciting light and the detecting light guided by the guide optical system onto a sample, detecting means that detects the detecting light passing through a thermal lens generated by the sample on which the exciting light has been irradiated, and analysis means that analyses the sample based on the detected detecting light, characterized by comprising an optical unit in which the guide optical system and the irradiation lens are disposed, the optical unit having an optical wave guide path as an optical path of the guide optical system.

In the second aspect of the present invention, it is preferable that the irradiation lens is fixed to an end of the optical wave guide path through which the exciting light and the detecting light are output.

In the second aspect of the present invention, it is preferable that the detecting light has a different frequency from that of the exciting light, and the irradiation lens has a chromatic aberration.

In the second aspect of the present invention, it is preferable that the irradiation lens comprises a gradient refractive index lens.

In the second aspect, it is preferable that the gradient refractive index lens is a solid-cylindrical rod lens.

In the second aspect, it is preferable that the optical wave guide path transmits the exciting light and the detecting light in a single mode.

In the second aspect, it is preferable that the optical unit has provided therein a light source for the exciting light and a light source for the detecting light.

In the second aspect, it is preferable that the optical unit has provided therein a channel disposed downstream of the irradiation lens in a direction of travel of the exciting light and the detecting light and through which a liquid containing the sample flows, and the detecting means disposed downstream of the channel in the direction of travel of the exciting light and the detecting light.

In the second aspect, it is preferable that the microchemical system comprises a channel-formed plate-shaped element disposed between the optical unit and the detecting means and having a channel through which a liquid containing the sample flows.

In the second aspect, it is preferable that the microchemical system comprises a parallel moving mechanism that moves the optical unit and the detecting means in parallel with a surface of the channel-formed plate-shaped element while maintaining relative positions of the optical unit and the detecting means.

BRIEF DESCRIPTION OF THE DRAWINGS

FIG. 7A shows a case in which the objective lens has chromatic aberration;

FIG. 7B shows a case in which the objective lens does not have chromatic aberration;

FIG. 8A shows a case in which the thermal lens is formed at a side close to the objective lens with respect to the focal position of the detecting light;

FIG. 8B shows a case in which the thermal lens is formed at a side remote from the objective lens with respect to the focal position of the detecting light.

DETAILED DESCRIPTION

Embodiments of a microchemical system according to the present invention will now be described with reference to the drawings.

Figure 1:
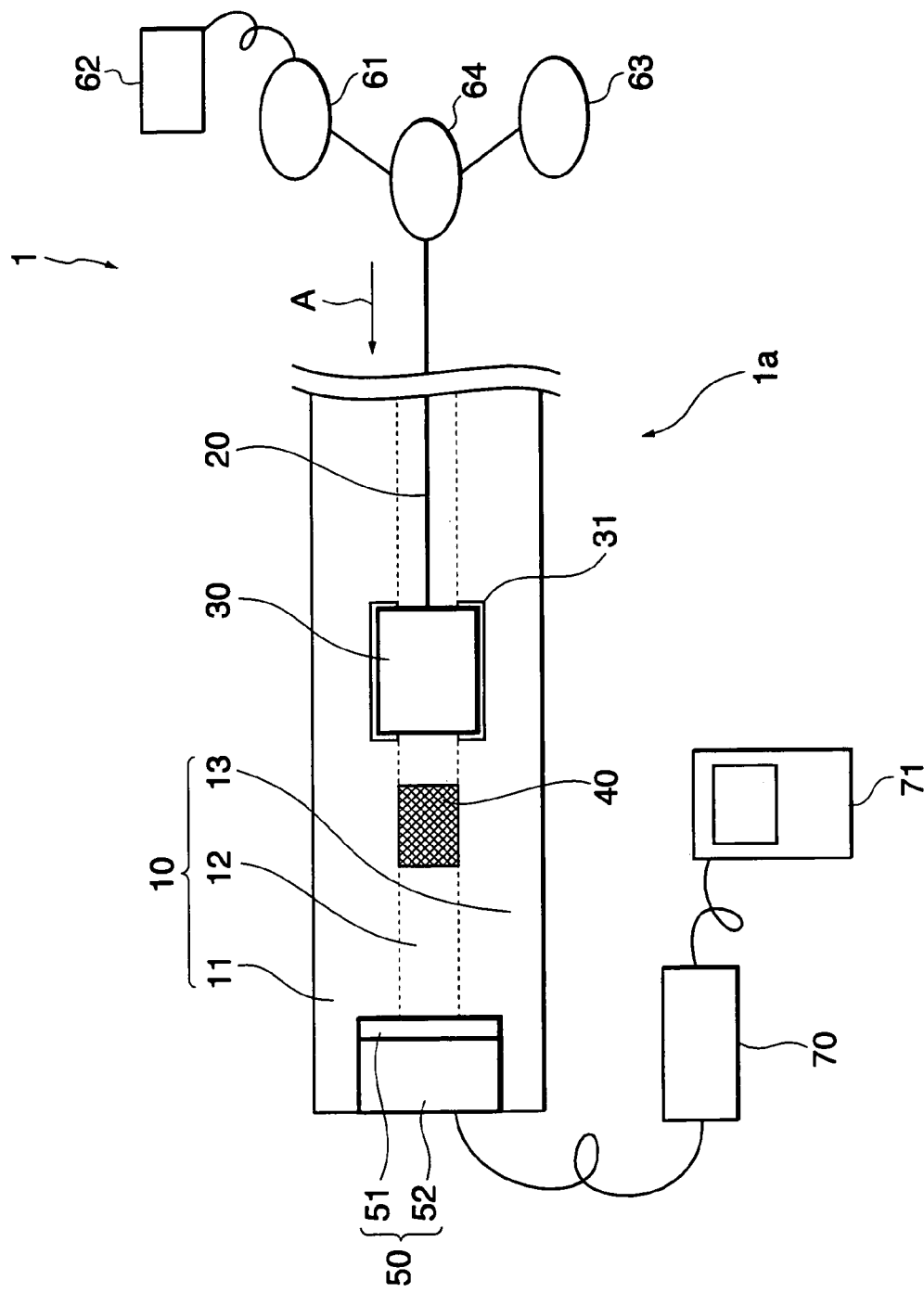
FIG. 1 is a schematic view showing the construction of a microchemical system according to a first embodiment of the present invention.

FIG. 1 is a schematic view showing the construction of a microchemical system according to a first embodiment of the present invention.

In FIG. 1, the microchemical system 1 includes an optical unit 1a which is comprised of a plate-shaped element 10 in which various component parts are provided. The plate-shaped element 10 is provided therein with an optical wave guide path 20 formed as an optical path for exciting light and detecting light, described later, an irradiation lens 30 disposed at a downstream end of the optical wave guide path 20 in a direction of travel of the exciting light and detecting light, indicated by the arrow A, for irradiating the exciting light and detecting light onto a sample, and a channel 40 disposed downstream of the irradiation lens 30 in the direction indicated by the arrow A, and through which a liquid containing the sample flows. A detector 50 is disposed at an end of the plate-shaped element 10 downstream of the channel 40 in the direction indicated by the arrow A. The optical wave guide path 20 is designed to transmit light in a single mode as the sole transmission mode.

The microchemical system 1 is further comprised of an exciting light source 61 such as a laser diode, that outputs the exciting light, a modulator 62 that modulates the exciting light, a detecting light source 63 such as a laser diode, that outputs the detecting light, an optical multiplexer 64 that coaxially aligns the exciting light and the detecting light, a lock-in amplifier 70 that synchronizes a detection signal received by the detector 50 with the modulator 62, and a computer 71 that analyzes an output signal from the lock-in amplifier 70. The exciting light and the detecting light that are aligned with each other by the optical multiplexer 64 are guided in the single mode by the optical wave guide path 20 to the irradiation lens 30.

The reason why the optical wave guide path 20 is of the single mode type is that in the case where a very small amount of solute in a sample is detected using the photothermal conversion spectroscopic analysis method, it is desirable that the exciting light should be as small as possible to obtain a great amount of energy used for the photothermal conversion, and a thermal lens having a small aberration should be generated by the exciting light.

The exciting light used to generate the thermal lens should desirably have a Gaussian distribution. Since light output from an optical fiber of the single mode type always has a Gaussian distribution, such an optical fiber is suitable for making the focal point of the exciting light small. If the thermal lens generated by the exciting light is small in size, it is desirable that the detecting light should also be limited to as small in diameter as possible to increase the number of detecting light beams passing the thermal lens to the maximum possible number. To this end, it is preferable that the exciting light and the detecting light are transmitted in the single mode.

The plate-shaped element 10 is comprised of glass substrates 11, 12 and 13 which are stacked upon one another in three layers. The plate-shaped element 10 is preferably made of glass in terms of durability and chemical resistance. In particular, in the case where living body samples such as cell samples are handled, for example, in the case where such samples are subjected to DNA analysis, the material is preferably a glass that has excellent acid resistance and alkali resistance, for example a borosilicate glass, a soda lime glass, an aluminoborosilicate glass, a quartz glass or the like. However, the plate-shaped element 10 may be made of an organic material such as a plastic for some specific usage.

Out of the glass substrates 11, 12 and 13, the intermediate glass substrate 12 is formed therein with the channel 40 through which flows a liquid containing a sample for mixing, agitating, synthesizing, separating, extracting or detecting the sample.

Out of the glass substrates 11, 12 and 13, the intermediate glass substrate 12 is formed therein with the optical wave guide path 20. The method for forming the optical wave guide path 20 is not limitative, and a flame hydrolysis method may be used, for example.

Figure 2:
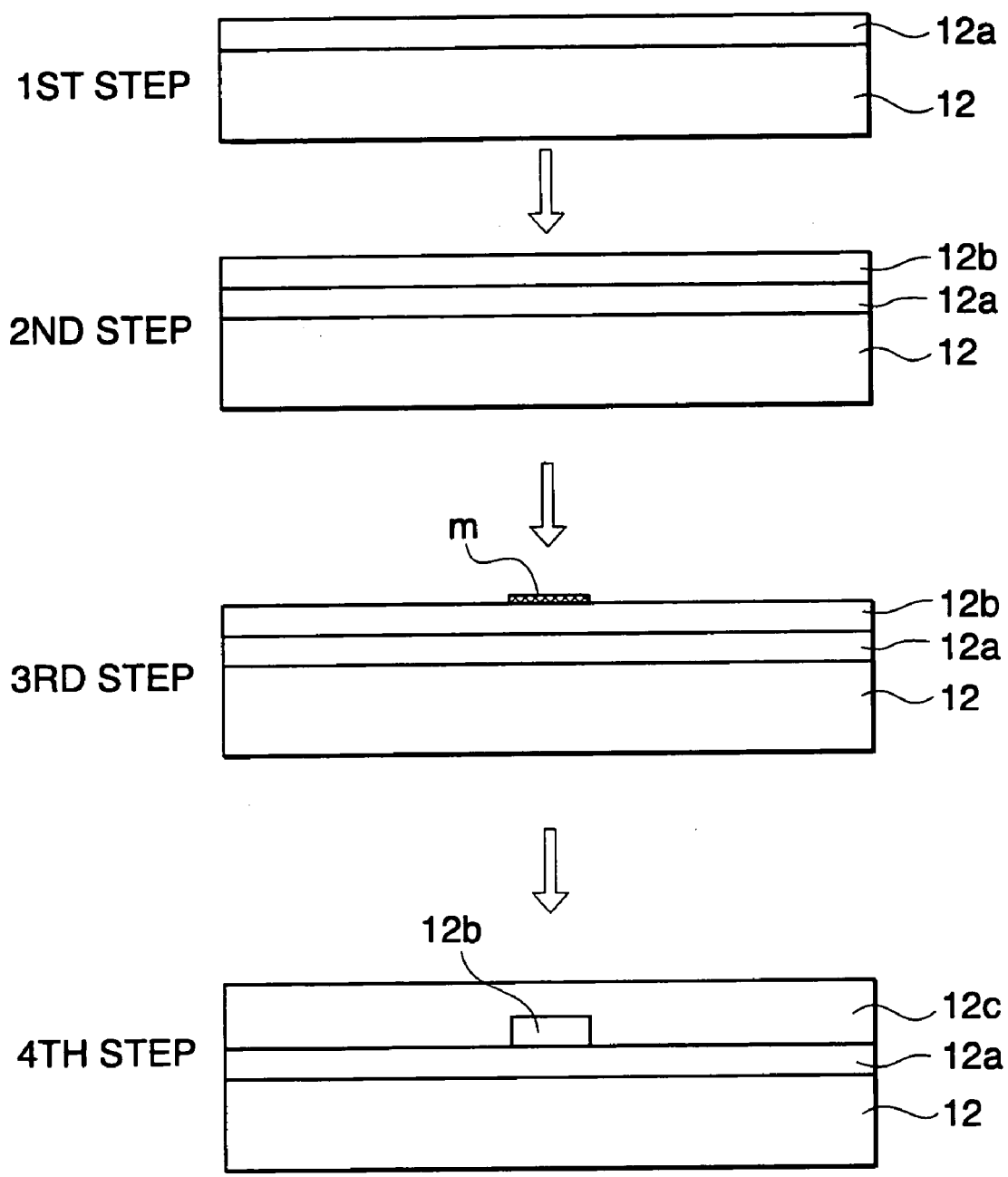
FIG. 2 is a view useful in explaining steps of forming an optical wave guide path by a flame hydrolysis method.

FIG. 2 is a view useful in explaining steps of forming an optical wave guide path by the flame hydrolysis method.

In a first step, silicon tetrachloride ($SiCl_4$) is subjected to a flame hydrolysis process to deposit a glass fine particle layer formed of $SiO_2$ for a clad on a surface of the glass substrate 12, and then the glass fine particle layer is heated to a high temperature to form a $SiO_2$ layer 12a. In a second step, a flame hydrolysis process is carried on silicon tetrachloride ($SiCl_4$) and germanium tetrachloride ($GeCl_4$) to deposit a glass fine particle layer formed of $SiO_2$ in which germanium (Ge) is doped on a surface of the $SiO_2$ layer 12a, and the glass fine particle layer is heated to a high temperature to form a Ge-doped $SiO_2$ layer 12b for a core. In a third step, a portion of a surface of the Ge-doped $SiO_2$ layer 12b which is to be left as a core is covered with a mask m. Then, photolithography and reactive etching are carried out to remove unnecessary portions of the Ge-doped $SiO_2$ layer 12b other than the portion thereof covered with the mask m. In a final or fourth step, a glass fine particle layer formed of $SiO_2$ is again deposited, followed by heating to a high temperature to form a $SiO_2$ layer 12c. In this way, a clad of the $SiO_2$ layers 12a, 12c and a core of the Ge-doped $SiO_2$ layer 12b surrounded by the clad are formed. The Ge-doped $SiO_2$ layer 12b has a higher refractive index than those of the surrounding $SiO_2$ layers 12a, 12c. Thus, an optical wave guide path is formed by the clad and the core. An example of formation of an optical wave guide path using the above described method is described in J. Lighywave Tech. Vol. 17(5)771 (1999).

In the above method for forming the optical wave guide path 20, if the glass substrate 12 has such a refractive index relative to the refractive index of the core 12b as to allow the glass substrate 12 to be used as the clad, the formation of the $SiO_2$ layer for the clad may be omitted.

The optical guide path 20 is formed in concentricity with a central line passing the centers of the irradiation lens 30 and the channel 40. Therefore, the portion of the glass substrate 12 in which the optical wave guide path 20 is to be formed may be removed to a suitable depth in advance by etching or the like, followed by forming the optical wave guide path 20 by the flame hydrolysis method.

The optical multiplexer 64 is connected to an end of the optical wave guide path 20 formed as above opposite to the end on the side of the irradiation lens 30. The exciting light source 61 and the detecting light source 63 are connected to the optical multiplexer 64. The modulator 62 is connected to the exciting light source 61. It may be arranged such that the exciting light and the detecting light are coaxially aligned with each other outside the optical wave guide path by a dichroic mirror or the like instead of using the optical multiplexer 64, before they are input to the optical wave guide path 20.

On the other hand, the end of the optical wave guide 20 on the irradiation lens 30 side reaches an irradiation lens housing 31 formed for accommodating the irradiation lens 30. The irradiation lens 30 accommodated in the irradiation lens housing 31 is a gradient refractive index rod lens. The irradiation lens 30 will be also hereinafter referred to as the rod lens 30.

The rod lens 30 is made of a cylindrical transparent member which has a refractive index continuously varying from the center to the periphery thereof and which is known as a converging light-transmitting body for which the refractive index n(r) at a position a distance r from the central axis in the radial direction is given approximately by the quadratic equation in r, $$n(r)=n_0\{1-(g^2/2)\cdot r^2\},$$

wherein $n_0$ represents the refractive index at the central axis, and g represents the square distribution constant.

If the length $z_0$ of the rod lens 30 is chosen to be in a range of $0<z_0<\pi/2$ g, then the image formation characteristics of the rod lens 30 will be the same as those of a normal convex lens, even though the both end faces of the rod lens 30 are flat; when a parallel light beam is incident on one end face of the rod lens 30, a focal point will be formed at a position a distance $s_0$ from the other end face of the rod lens 30 from which the light beam exits, where $$s_0=cot(gz_0)/n_0 g.$$

The rod lens 30 may be manufactured, for example, by the following method.

A rod-shaped element is formed from a glass having 57 to 63 mol % of $SiO_2$, 17 to 23 mol % of $B_2O_3$, 5 to 17 mol % of $Na_2O$, and 3 to 15 mol % of $Tl_2O$ as principal components. This glass rod element is then treated in an ion exchange medium such as a potassium nitrate salt bath, thus carrying out ion exchange between thallium ions and sodium ions in the glass and potassium ions in the medium, and hence generates in the glass rod element a refractive index distribution in which the refractive index decreases continuously from the center of the glass rod element toward the periphery thereof.

The rod lens 30 accommodated in the irradiation lens housing 31 is designed such that the focal position of the detecting light is shifted slightly by an amount $\Delta L$ relative to the focal position of the exciting light.

The confocal length Ic (nm) is given by $Ic=\pi\cdot(d/2)^2/\lambda_1$, wherein d represents the Airy disk and is given by $d=1.22\times \lambda_1/NA$, $\lambda_1$ represents the wavelength (nm) of the exciting light, and NA represents the numerical aperture of the rod lens 30. When the exciting light and the detecting light are guided by the optical wave guide path 20, the numeral aperture of output light of the optical wave guide path 20 is small, and therefore, if a rod lens having a large numerical aperture is used, calculations must be carried out using the numerical aperture of the optical wave guide path 20.

The $\Delta L$ value described above varies according to the thickness of the sample to be analyzed. When carrying out measurements on a sample having a thickness lower than the confocal length, it is preferable for the $\Delta L$ value to be $Ic<\Delta L<10\cdot Ic$, but most preferably, $\Delta L$ should be equal to $\sqrt{3}\cdot Ic$.

Figure 3:
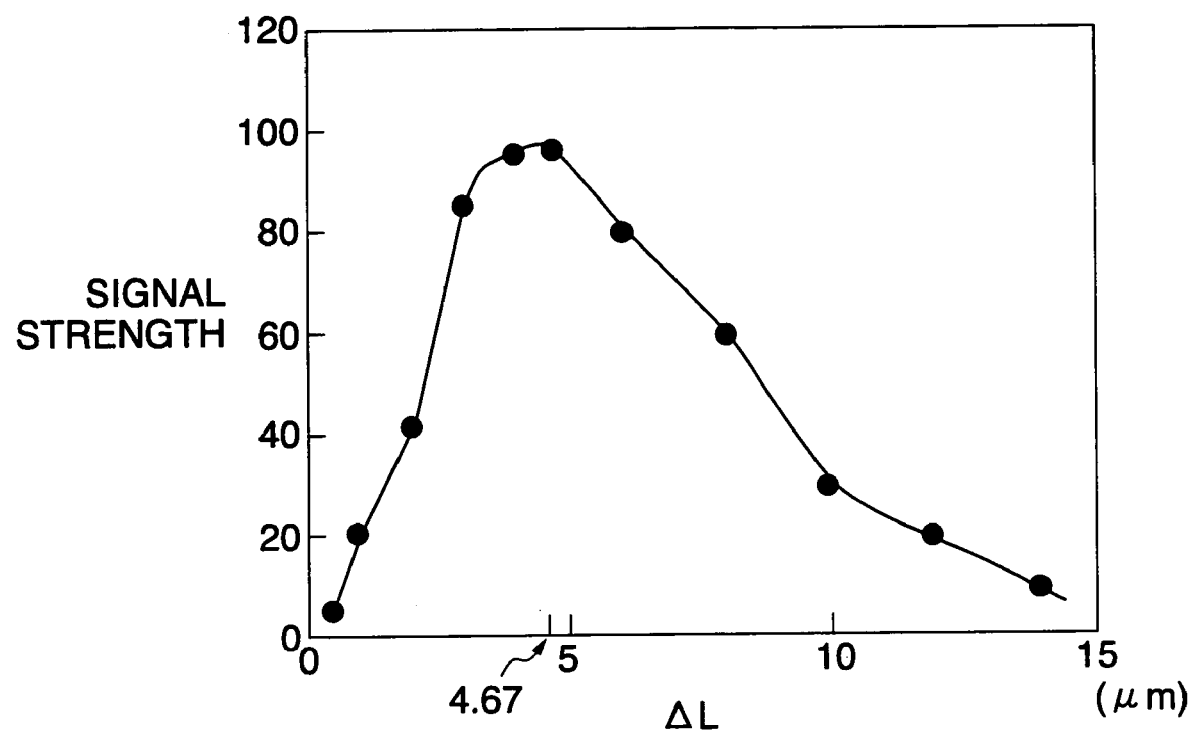
FIG. 3 is a graph useful in explaining a change in signal strength relative to a shift ΔL from the optimum focal position of a rod lens.

For example, if NA=0.46, $\lambda_1$=488 nm and $\lambda_2$=632.8 nm, then the relationship between the shift $\Delta L$ value and the signal strength is as shown in FIG. 3. FIG. 3 shows the signal strength relative to the value at $\Delta L$=4.67 μm, with the value at $\Delta L$=4.67 μm being taken to be 100. It can be seen from FIG. 3 that the signal strength is a maximum at $\Delta L$=4.67 μm. It is thus preferable to design the rod lens 30 such that the shift $\Delta L$ is the value of 4.67 μm with the above two wavelengths assuming the above values. $\Delta L$ represents the difference between the focal position of the detecting light and the focal position of the exciting light, and the same result is achieved regardless of whether the focal distance of the detecting light is longer or shorter than the focal distance of the exciting light.

The exciting light and the detecting light having passed through the rod lens 30 are irradiated onto a sample in the channel 40. Part of the exciting light that is irradiated is absorbed by the sample. The sample that has absorbed the exciting light rises in temperature to produce a thermal lens effect. The exciting light and the detecting light that have passed through the sample having produced the thermal lens effect are detected by the detector 50 disposed at the end of the plate-shaped element 10.

The detector 50 is mounted in the end of the plate-shaped element 10, and is comprised of a wavelength filter 51 close to the channel 40, and a photoelectric transducer 52 disposed in series to the wavelength filter 51. The wavelength filter 51 selectively allows only the detecting light, out of the exciting light and the detecting light that have passed through the thermal lens generated by the sample, to pass therethrough. A pin hole for passing only part of the detecting light may be provided upstream of the photoelectric transducer 52 in the direction indicated by the arrow A.

A detection signal obtained through detection of the detecting light by the photoelectric transducer 52 is delivered to the lock-in amplifier 72 for synchronizing the detection signal with the modulator 62. Then, the delivered detection signal is analyzed by the computer 71.

The detector 50 may be disposed within the plate-shaped element 10 or may be mounted in the end face of the plate-shaped element 10.

The optical multiplexer 64, exciting light source 61, modulator 62 and detecting light source 63 may be formed in one body with the plate-shaped element 10, whereby the microchemical system 1 can be made compact in size.

Figure 4:
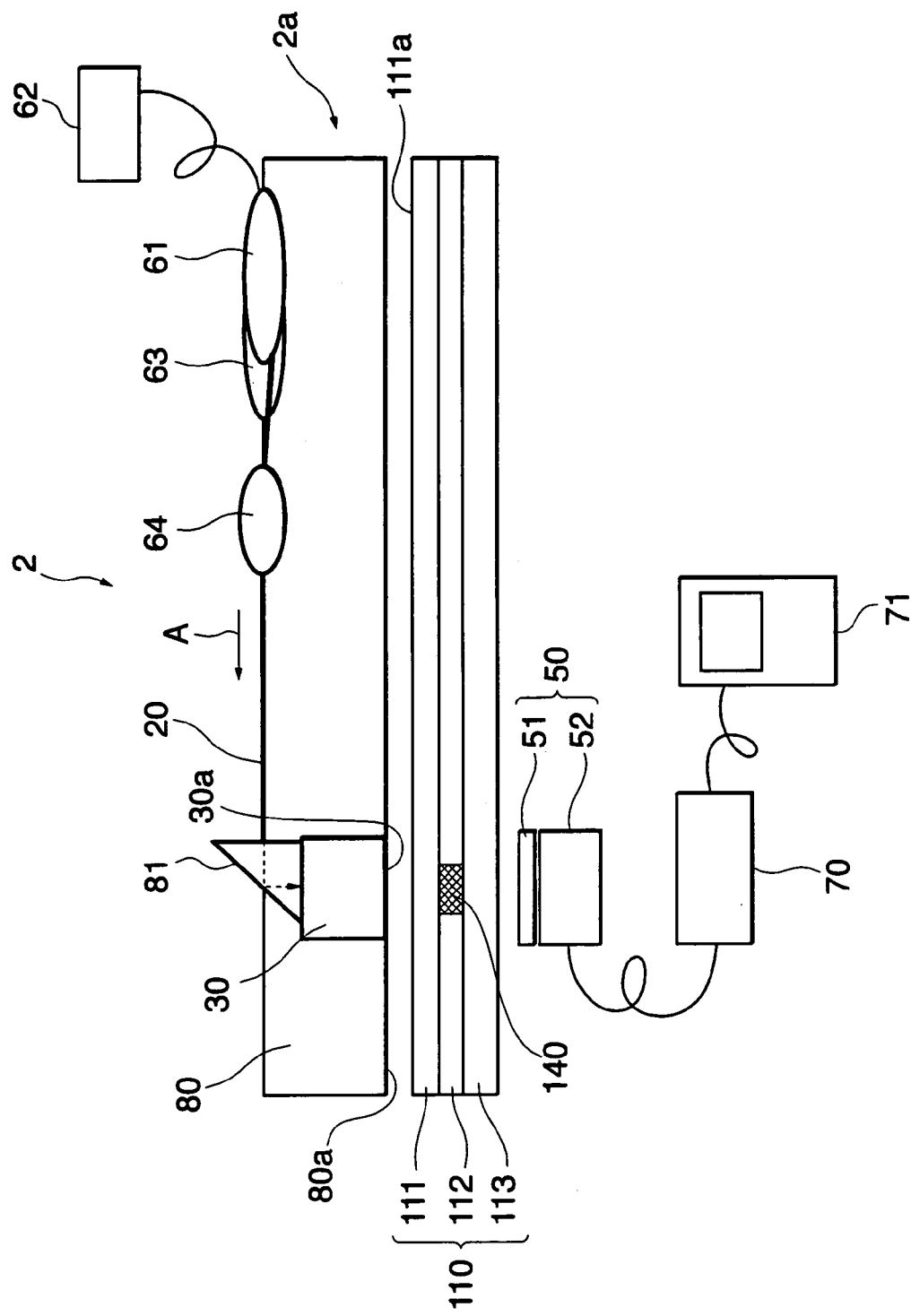
FIG. 4 is a schematic view showing the construction of a microchemical system according to a second embodiment of the present invention.

FIG. 4 is a schematic view showing the construction of a microchemical system according to a second embodiment of the present invention.

In FIG. 4, elements and parts of the microchemical system 2 according to the second embodiment corresponding to those of the microchemical system 1 according to the first embodiment are designated by identical reference numerals, description of which is omitted. The microchemical system 2 according to the present embodiment includes an exciting light source 61, a detecting light source 63, and others, and further includes an optical unit 2a which is comprised of a plate-shaped element 80 having an optical wave guide path 20 formed therein.

Out of ends of the optical wave guide path 20, a downstream end thereof in a direction indicated by the arrow A is directed toward a prism 81. The end of the optical wave guide path 20 may be disposed in contact with the prism 81. The exciting light and the detecting light that are input to the prism 81 through the end of the optical wave guide path 20 are changed in traveling direction to a downward side as viewed in the space of FIG. 4 inside the prism 81. A gradient refractive index rod lens 30 has an end face thereof disposed in contact with a surface of the prism 81 through which the exciting light and the detecting light having changed in traveling direction are output. The other end face 30a of the rod lens 30 extends parallel with a major surface 80a of the plate-shaped element 80. The end face 30a of the rod lens 30 may be flush with the major surface 80a of the plate-shaped element 80.

A channel corresponding to the channel 40 of the microchemical system according to the second embodiment is not formed in the plate-shaped element 80. Instead, a channel through which a liquid containing a sample flows is formed in a channel-formed plate-shaped element 110 which is a separate member from the plate-shaped element 80. As is the case with the plate-shaped element 10 of the first embodiment, the channel-formed plate-shaped element 110 is comprised of three glass substrates 111, 112, and 113 stacked one upon another, with the intermediate glass substrate 112 having a channel 140 formed therein.

The channel-formed plate-shaped element 110 and the plate-shaped element 80 extend parallel with each other. The focal position of the exciting light output from the rod lens 30 lies within the channel 140. The end face 30a of the rod lens 30 from which the exciting light is output may be disposed in contact with the opposed surface of the channel-formed plate-shaped element 110 (the surface 111a of the glass substrate 111) or may be spaced therefrom.

If the two members are disposed in contact with each other, a glass substrate 111 having a thickness suitable for the focal distance of the rod lens 30 may be used such that the focal position of the rod lens 30 can be located within the channel 140. If the glass substrate 111 has an insufficient thickness, a spacer for adjustment of the focal distance may be interposed between the rod lens 30 and the glass substrate 111. These methods do not require an operation of adjusting the focal distance, to thereby contribute to improvement of the working efficiency of the user. Besides, a device for adjusting the focal distance is not required, thereby making it possible to design the microchemical system compact in size and reduce the cost.

The exciting light and the detecting light output from the rod lens 30 pass through the sample in the channel 140 and are then detected by the detector 50 disposed below the channel-formed plate-shaped element 110. A detection signal is output from the detector 50 and passes through the lock-in amplifier 70 to be analyzed by the computer 71.

Figure 5:
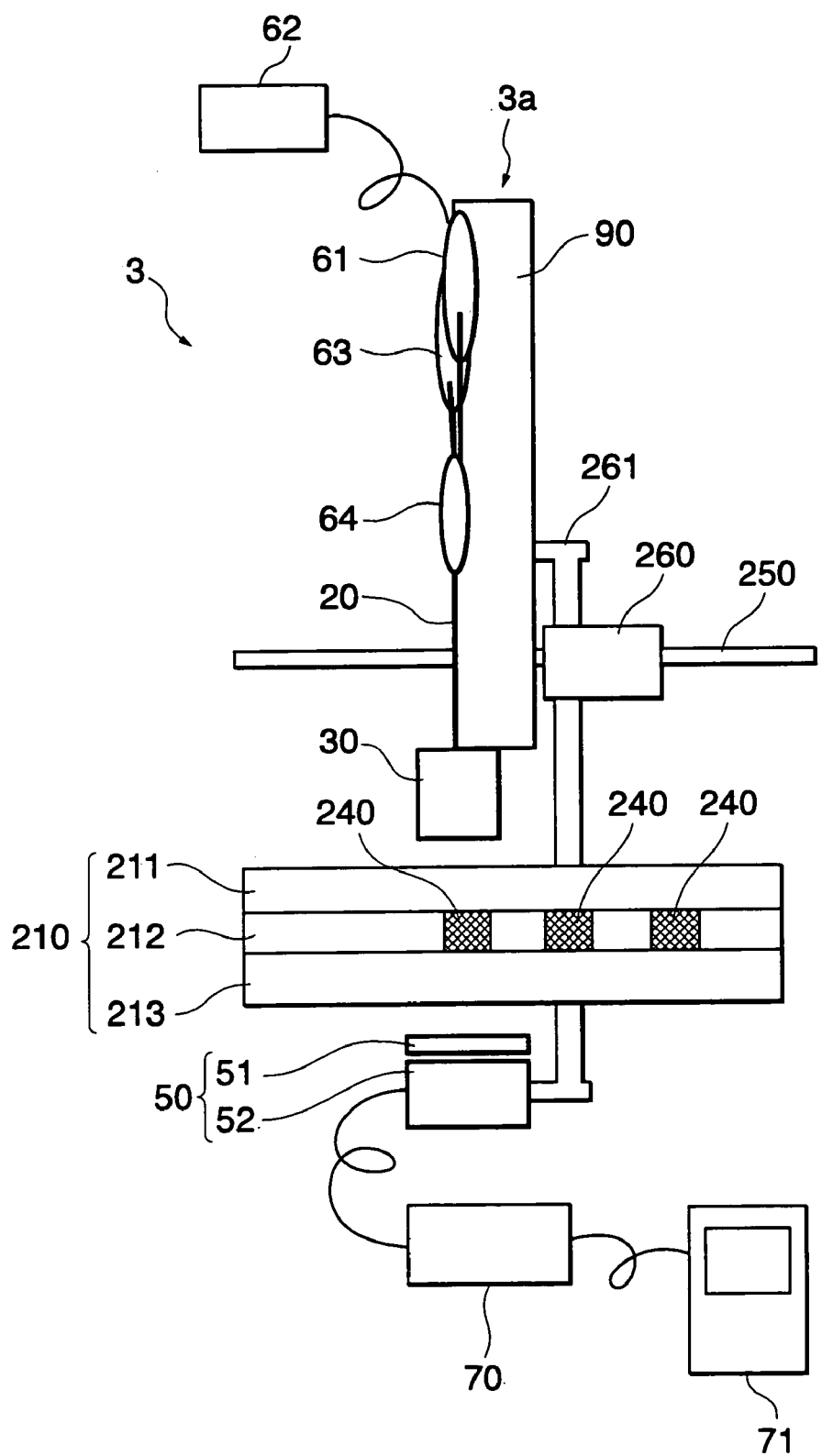
FIG. 5 is a schematic view showing the construction of a microchemical system according to a third embodiment of the present invention.
Figure 6:
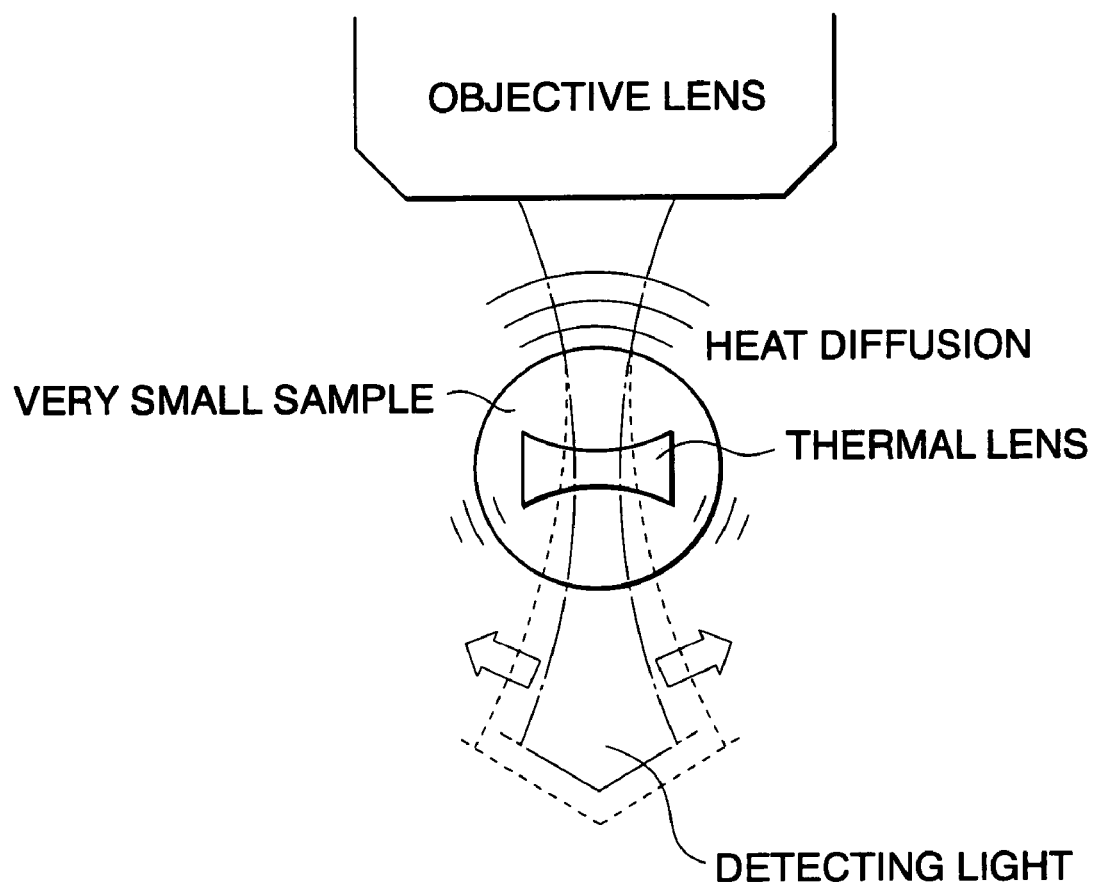
FIG. 6 is a view useful in explaining the principle of a thermal lens.
Figure 7A:
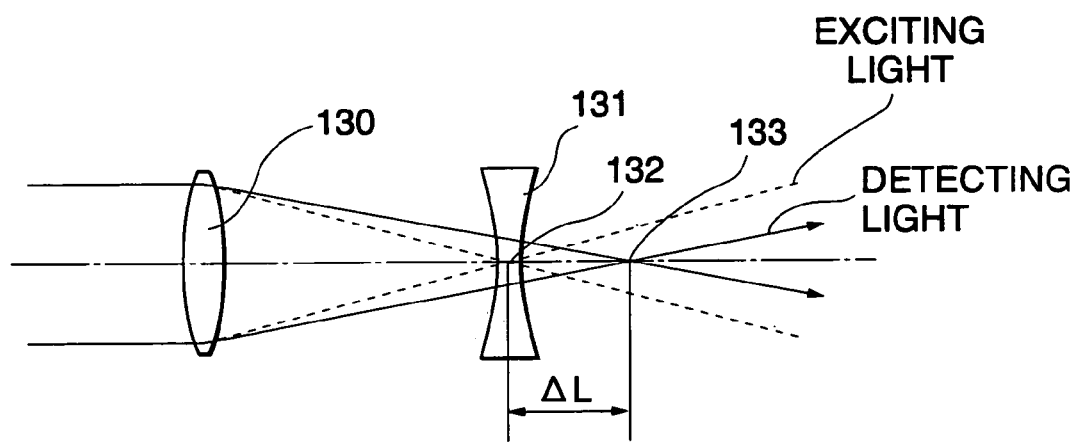
FIGS. 7A and 7B are views useful in explaining the formation position of a thermal lens and the focal position of detecting light in the direction of travel of exciting light; specifically.
Figure 7B:
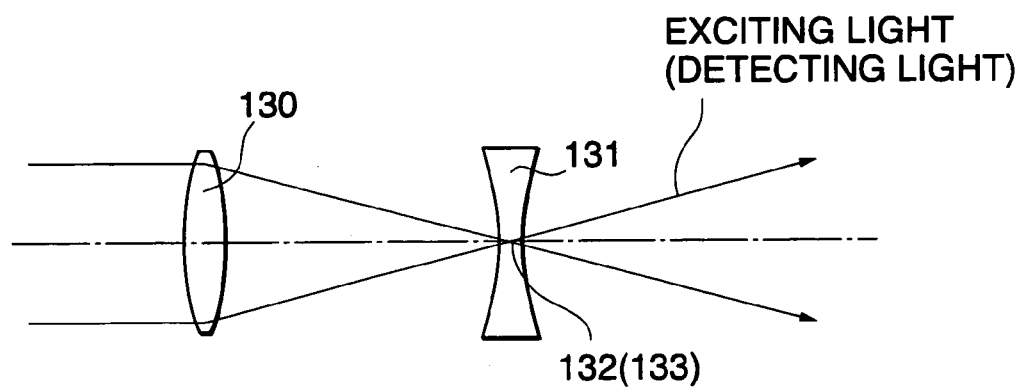
Figure 8A:
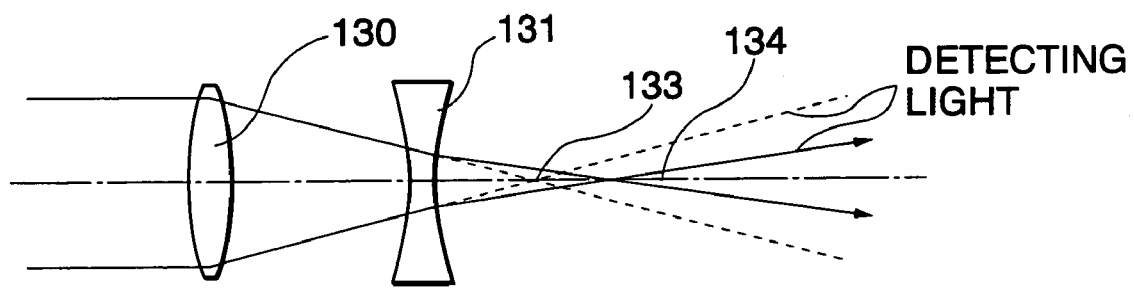
FIGS. 8A and 8B are views useful in explaining the formation position of a thermal lens and the focal position of detecting light in the direction of travel of exciting light; specifically.
Figure 8B:
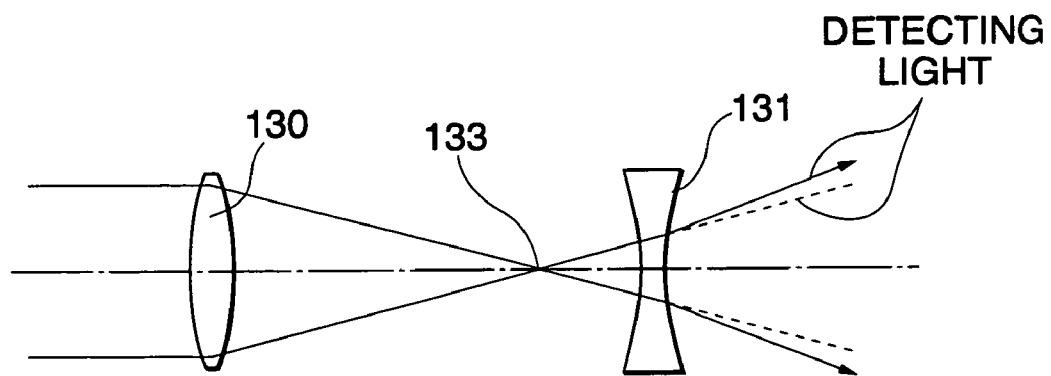
Figure 9:
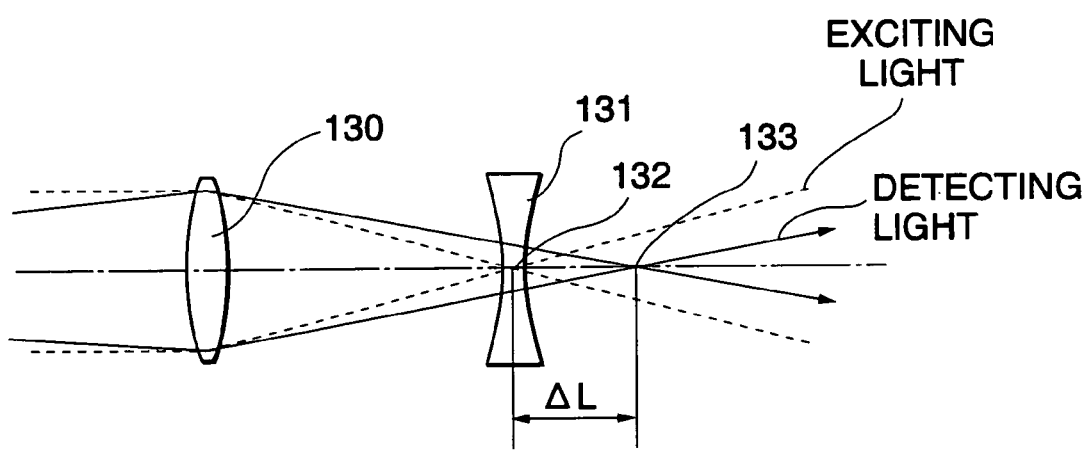
FIG. 9 is a view useful in explaining a method of detecting changes in refractive index within a thermal lens in a conventional photothermal conversion spectroscopic analyzer in the case that the detecting light is diverged using a diverging lens.

FIG. 5 is a schematic view showing the construction of a microchemical system according to a third embodiment of the present invention.

In FIG. 5, elements and parts of the microchemical system 3 according to the third embodiment corresponding to those of the microchemical system 1 according to the first embodiment and the microchemical system 2 according to the second embodiment are designated by identical reference numerals, description of which is omitted. The microchemical system 3 according to the present embodiment includes an exciting light source 61, a detecting light source 63, and others, and further includes an optical unit 3a which is comprised of a plate-shaped element 90 having an optical wave guide path 20 formed therein.

Mounted on one end of the plate-shaped element 90 is a gradient refractive index rod lens 30 which is disposed with its optical axis in alignment with the direction in which the optical wave guide path 20 extends. The plate-shaped element 90 is disposed such that the end thereof on which the gradient refractive rod lens is mounted is located downward. The rod lens 30 may have one end thereof disposed in contact with a downstream end of the optical wave guide path 20 that guides the exciting light and the detecting light. The rod lens 30 may be housed in the plate-shaped element 90.

A plate-shaped element 210 is disposed below the rod lens 30. The rod lens 30 and the plate-shaped element 210 are disposed such that an end face of the rod lens 30 and an opposed surface of the plate-shaped element 210 extend parallel with each other. The plate-shaped element 210 is formed therein with a plurality of channels 240 through which a liquid containing a sample flows. The plate-shaped element 210 is comprised of three glass substrates 211, 212 and 213 stacked one upon another, with the channels 240 formed in the intermediate glass substrate 212.

An XY stage (parallel moving mechanism) having a stage 250 is disposed parallel with the other surface of the channel-formed plate-shaped element 210. The stage 250 has mounted thereon a carrier 260 which is guided to move parallel with the channel-formed plate-shaped element 210. Fixed to the carrier 260 is a jig 261 which crosses the stage 250 and extends in a direction perpendicular to the channel-formed plate-shaped element 210. The jig 261 has an upper end thereof located above the channel-formed plate-shaped element 210 and a lower end below the same. The plate-shaped element 90 is secured to the upper end of the jig 261, and a detector 50 which has a light receiving portion, not shown, directed toward the plate-shaped element 210 is secured to the lower end of the jig 261.

With this arrangement, as the carrier 260 is moved along the stage 250, the rod lens 30 and the detector 50 move parallel with the respective opposed surfaces of the channel-formed plate-shaped element 210 while maintaining respective relative positions. By causing thee rod lens 30 and the detector 50 to move by this XY stage, it is possible to measure the sample in the channels 240 formed in the plate-shaped element 210 at desired measuring points.

INDUSTRIAL APPLICABILITY

As described above in detail, according to the photothermal conversion spectroscopic analysis method of the present invention, the exciting light and the detecting light are guided in a single mode to the irradiation lens via an optical wave guide path. Therefore, the exciting light and the detecting light can be always maintained in coaxially aligned relation. As a result, it is not necessary to adjust the optical axes of the exciting light and the detecting light relative to each other, to thereby enable the working efficiency of the user to be improved.

As described above in detail, according to the microchemical system of the present invention, an optical unit is provided in which the guide optical system and the irradiation lens are disposed, the optical unit having an optical wave guide path as an optical path of the guide optical system. Therefore, the exciting light and the detecting light can be always maintained in coaxially aligned relation. As a result, it is not necessary to adjust the optical axes of the exciting light and the detecting light relative to each other, to thereby enable the working efficiency of the user to be improved. Further, since a device for optical axis adjustment is not required, the microchemical system can be designed compact in size.

According to the microchemical system of the present invention, the irradiation lens is fixed to an end of the optical wave guide path through which the exciting light and the detecting light are output. Therefore, the optical axes of all of the exciting light and the detecting light as well as the irradiation lens can be fixed in position. As a result, the optical axis adjustment is not required, enabling the working efficiency of the user to be positively improved. Further, since a jig for optical axis adjustment or the like is not required, the microchemical system can be positively designed compact in size.

According to the microchemical system of the present invention, the detecting light has a different frequency from that of the exciting light, and the irradiation lens has a chromatic aberration. The focal positions of the exciting light and the detecting light can be shifted without using an external optical system, to thereby enable the microchemical system to be designed more compact in size.

According to the microchemical system of the present invention, the irradiation lens comprises a gradient refractive index lens. Therefore, the irradiation lens can be made smaller in size. This leads to the possibility that the microchemical system is designed more compact in size.

According to the microchemical system of the present invention, the gradient refractive index lens is a solid-cylindrical rod lens. As a result, it is easy to carry the gradient refractive index lens.

According to the microchemical system of the present invention, the optical wave guide path transmits the exciting light and the detecting light in a single mode. Therefore, the thermal lens generated by the exciting light can have a reduced aberration. As a result, measurements can be achieved with higher accuracy.

According to the microchemical system of the present invention, the optical unit has provided therein a light source for the exciting light and a light source for the detecting light. Therefore, it is not necessary to provide a space for installing the exciting light source and the detecting light source outside the optical unit, to thereby ensure that the microchemical system can be designed more compact in size.

According to the microchemical system of the present invention, the optical unit has provided therein a channel through which a liquid containing the sample flows, and the detecting means. It is, therefore, not necessary to provide a space for installing a channel-formed element and the detecting means outside the optical unit, to thereby ensure that the microchemical system can be designed more compact in size.

According to the microchemical system of the present invention, the microchemical system comprises a channel-formed plate-shaped element disposed between the optical unit and the detecting means and having a channel through which a liquid containing the sample flows. This can facilitate replacement of the channel-formed plate-shaped element with a new one.

According to the microchemical system of the present invention, a parallel moving mechanism can move the optical unit and the detecting means in parallel with a surface of the channel-formed plate-shaped element while maintaining relative positions of the optical unit and the detecting means. This can dispense with the need to move the channel-formed plate-shaped element when changing the measuring position. As a result, the user need not wait for any time period until the sample in the channel becomes stationary if the channel-formed plate-shaped element were moved, to thereby enable the measure to be carried out quickly. This leads to further enhanced working efficiency of the user. Further, since the relative positions of the optical unit and the detecting means are maintained, no mechanism for adjusting the relative positions is required, to thereby ensure that the microchemical system can be designed more compact in size.

The invention claimed is:

1. A microchemical system comprising:
   an exciting light source that outputs exciting light;
   a detecting light source that outputs detecting light;
   an optical unit comprising an optical waveguide that guides the exciting light and the detecting light together, and an irradiation lens that irradiates the exciting light and the detecting light guided by said optical waveguide path onto a sample;
   detecting means for detecting the detecting light passing through a thermal lens generated by the sample on which the exciting light has been irradiated; and
   analysis means for analyzing the sample based on the detected detecting light;
   wherein said optical unit further comprises a channel disposed downstream of said irradiation lens in a direction of travel of the exciting light and the detecting light and through which a liquid containing the sample flows, and said detecting means is disposed downstream of the channel in the direction of travel of the exciting light and the detecting light.

2. A microchemical system comprising:
   an exciting light source that outputs exciting light;
   a detecting light source that outputs detecting light;
   an optical unit comprising an optical waveguide that guides the exciting light and the detecting light together, and an irradiation lens that irradiates the exciting light and the detecting light guided by said optical waveguide path onto a sample;
   detecting means for detecting the detecting light passing through a thermal lens generated by the sample on which the exciting light has been irradiated;
   analysis means for analyzing the sample based on the detected detecting light; and a channel-formed plate-shaped element disposed between the optical unit and the detecting means and having a channel through which a liquid containing the sample flows.

3. A microchemical system as claimed in claim 2, further comprising a parallel moving mechanism that moves said optical unit and said detecting means in parallel with a surface of said channel-formed plate-shaped element while maintaining relative positions of said optical unit and said detecting means.

4. A microchemical system as claimed in claim 1, wherein said irradiation lens is fixed to an end of the optical wave guide path through which the exciting light and the detecting light are output.

5. A microchemical system as claimed in claim 1, wherein the detecting light has a different frequency than the exciting light, and said irradiation lens has a chromatic aberration.

6. A microchemical system as claimed in claim 1, wherein the detecting light has a different frequency than the exciting light, and said irradiation lens has a chromatic aberration.

7. A microchemical system as claimed in claim 2, wherein said irradiation lens is fixed to an end of the optical wave guide path through which the exciting light and the detecting light are output.

8. A microchemical system as claimed in claim 2, wherein the detecting light has a different frequency than the exciting light, and said irradiation lens has a chromatic aberration.

9. A microchemical system as claimed in claim 2, wherein the detecting light has a different frequency than the exciting light, and said irradiation lens has a chromatic aberration.

* * * * *